United States Patent
Teng et al.

(10) Patent No.: US 11,844,589 B2
(45) Date of Patent: Dec. 19, 2023

(54) MULTI-SENSOR SYSTEM FOR CARDIOVASCULAR AND RESPIRATORY TRACKING

(71) Applicant: QUALCOMM Incorporated, San Diego, CA (US)

(72) Inventors: Diyan Teng, Santa Clara, CA (US); Mehul Soman, San Jose, CA (US); Rashmi Kulkarni, Redwood City, CA (US)

(73) Assignee: QUALCOMM Incorporated

( * ) Notice: Subject to any disclaimer, the term of this patent is extended or adjusted under 35 U.S.C. 154(b) by 159 days.

(21) Appl. No.: 17/302,444

(22) Filed: May 3, 2021

(65) Prior Publication Data

US 2022/0346653 A1    Nov. 3, 2022

(51) Int. Cl.
*A61B 5/0205*    (2006.01)
*A61B 5/18*    (2006.01)

(52) U.S. Cl.
CPC .............. *A61B 5/0205* (2013.01); *A61B 5/18* (2013.01); *A61B 2562/0219* (2013.01); *A61B 2562/0257* (2013.01); *A61B 2562/046* (2013.01)

(58) Field of Classification Search
CPC ................................. A61B 5/0205; A61B 5/18
USPC ........................................................... 701/36
See application file for complete search history.

(56) References Cited

U.S. PATENT DOCUMENTS

2016/0152180 A1* 6/2016 Kirsch ..................... B60Q 1/52
701/36
2016/0302715 A1    10/2016 Larson et al.
2022/0087540 A1*  3/2022 Marcolino Quintao
Severgnini ............... A61B 5/25

FOREIGN PATENT DOCUMENTS

| WO | WO-2013037399 A1 * | 3/2013 | ............ A61B 5/024 |
|---|---|---|---|
| WO | WO2013037399 A1 | 3/2013 | |
| WO | WO2015174963 A1 | 11/2015 | |
| WO | WO2016038148 A1 | 3/2016 | |
| WO | WO2020202159 A1 | 10/2020 | |

OTHER PUBLICATIONS

International Search Report and Written Opinion—PCT/US2022/071292—ISA/EPO—dated Sep. 5, 2022.
Alizadeh M., et al., "Remote Monitoring of Human Vital Signs Using mm-Wave FMCW Radar", Special Section on Advanced Information Sensing And Learning Technologies for Data-Centric Smart Health Applications, vol. 7, Apr. 23, 2019, pp. 54958-54968.

(Continued)

*Primary Examiner* — Peter D Nolan
*Assistant Examiner* — Luke Huynh
(74) *Attorney, Agent, or Firm* — QUALCOMM Incorporated (57) ABSTRACT

Cardiovascular or respiratory data of a subject is measured using a multi-sensor system. The multi-sensor system includes a mm-wave FMCW radar sensor, an IMU sensor, and one or more proximity sensors. The mm-wave FMCW radar sensor may be selected and its view angle adjusted based on positioning data regarding the subject obtained from the one or more proximity sensors. Each of the mm-wave FMCW radar sensor and the IMU sensor may acquire cardiovascular or respiratory measurements of the subject, and the measurements may be fused for improved accuracy and performance.

10 Claims, 6 Drawing Sheets

(56) References Cited

OTHER PUBLICATIONS

Bruser C., et al., "Adaptive Beat-to-Beat Heart Rate Estimation in Ballistocardiograms", IEEE Transactions on Information Technology In Biomedicine, vol. 15, No. 5, Sep. 2011, pp. 778-786.
Culjak I., et al., "A Data-Fusion Algorithm for Respiration Rate Extraction Based on UWB Transversal Propagation Method", 2020 IEEE International Instrumentation and Measurement Technology Conference (I2MTC), IEEE, May 25, 2020, pp. 1-5, XP033785719, DOI: 10.1109/I2MTC43012.2020.9128628 [retrieved on Jun. 29, 2020], Section II-III, p. 2-p. 4; figures 1-5.
Ha U., et al., "Contactless Seismocardiography via Deep Learning Radars", Proceedings of the 26th Annual International Conference on Mobile Computing and Networking, ACMPUB27, New York, NY, USA, Sep. 21, 2020, pp. 1-14, XP058479977, DOI: 10.1145/3372224.3419982, ISBN: 978-1-4503-7085-1, Section 3-5, p. 829-p. 835, figures 1-13.
Migliorini M., et al., "Monitoring Nocturnal Heart Rate with Bed Sensor", Focus Theme—Original Articles, Methods Inf Med Apr. 2014; 53(04), pp. 308-313.
Partial International Search Report—PCT/US2022/071292—ISA/EPO—dated Jul. 7, 2022.
Sacco G., et al., "An FMCW Radar for Localization and Vital Signs Measurement for Different Chest Orientations", Sensors 2020, 20, 3489; doi:10.3390/s20123489, Jun. 20, 2020, pp. 1-14.

\* cited by examiner

MULTI-SENSOR SYSTEM FOR CARDIOVASCULAR AND RESPIRATORY TRACKING

TECHNICAL FIELD

This disclosure relates generally to tracking physiological data and more particularly to tracking cardiovascular and respiratory data using millimeter-wave radar sensors such as millimeter-wave frequency modulated continuous wave (FMCW) radar sensors.

DESCRIPTION OF RELATED TECHNOLOGY

Monitoring human vital signs is very critical to saving lives. In many cases there is a need for continuous surveillance of an individual or detecting the presence of an individual by measuring vital signs. Tracking physiological data such as heart rate and breathing rate can be imperative in many contexts such as monitoring patients in a clinical setting, measuring fitness levels, detecting driver fatigue, studying sleep, searching for survivors after a natural disaster, and many more.

Typically, electronic sensing of heart rate and breathing rate is performed using wires or cables. In such instances, wires or cables are connected from a sensor attached to the human body. Alternatively, electronic sensing of heart rate and breathing rate can be performed using an elastic band. Electronic signals are sent to a processing system for analyzing the signals as a heart rate, breathing rate, pulse rate, etc. However, contact-based sensors may be difficult to implement, impractical, inconvenient, and obtrusive.

Various approaches have been proposed for contactless sensing of heart rate and breathing rate. One approach is to use optical interferometry, but a limitation of such an optical-based approach is that optical signals can be blocked by clothes or other materials. Another approach is to use ultrasonic waves to detect motion. However, a limitation of such an approach is poor signal-to-noise ratio as a result of low reflection.

SUMMARY

The devices, systems, and methods of this disclosure each have several aspects, no single one of which is solely responsible for the desirable attributes disclosed herein.

One aspect of the subject matter of this disclosure can be implemented in a multi-sensor system. The multi-sensor system includes a mm-wave FMCW radar sensor in an interior of a vehicle, where the mm-wave FMCW radar sensor is configured to obtain a first cardiovascular or respiratory measurement of a subject. The multi-sensor system further includes a first inertial measurement unit (IMU) sensor positioned in the interior of the vehicle, where the first IMU sensor is configured to obtain a second cardiovascular or respiratory measurement of the subject, and a second IMU sensor positioned in the interior of the vehicle, where the second IMU sensor is configured to obtain motion data associated with the vehicle. The multi-sensor system further includes one or more proximity sensors configured to identify a location of a subject's chest inside the vehicle.

In some implementations, the mm-wave FMCW radar sensor is configured to transmit signals towards the location of the subject's chest. In some implementations, the first IMU sensor is positioned in a seat, positioned on an outer surface of the seat, or positioned underneath the seat of the vehicle. In some implementations, the second IMU sensor is positioned on a steering wheel or dashboard of the vehicle. In some implementations, the one or more proximity sensors comprise an array of capacitive proximity sensors. In some implementations, the multi-sensor system further includes a control system communicatively connected to the mm-wave FMCW radar sensor, the first IMU sensor, the second IMU sensor, and the one or more proximity sensors, where the control system is configured to: determine the location of the subject's chest relative to the mm-wave FMCW radar sensor using the one or more proximity sensors, and adjust a view angle of the mm-wave FMCW radar sensor to be directed towards the location of the subject's chest. In some implementations, the control system is further configured to: consolidate the first cardiovascular or respiratory measurement, the second cardiovascular or respiratory measurement, and the motion data associated with the vehicle to obtain an optimal cardiovascular or respiratory measurement. In some implementations, the multi-sensor system further includes a plurality of mm-wave FMCW radar sensors for obtaining multiple cardiovascular or respiratory measurements from multiple subjects in the interior of the vehicle, each of the cardiovascular or respiratory measurements being calculated to determine a subject's stress level, level of drowsiness, or health, and a control system communicatively connected to the plurality of mm-wave FMCW radar sensors, where the control system is configured to perform an action in the vehicle in response to the subject's stress level, level of drowsiness, or health.

Another innovative aspect of the subject matter described in this disclosure can be implemented in a multi-sensor system. The multi-sensor system includes one or more mm-wave FMCW radar sensors in a room, where the mm-wave FMCW radar sensor is configured to obtain a first cardiovascular or respiratory measurement of a subject in the room. The multi-sensor system further includes an IMU sensor in the room, where the IMU sensor is configured to obtain a second cardiovascular or respiratory measurement of the subject, and one or more proximity sensors configured to identify a body orientation of the subject inside the room.

In some implementations, at least one of the one or more mm-wave FMCW radar sensors is configured to be selected to obtain the first cardiovascular or respiratory measurement of the subject based on the body orientation of the subject. In some implementations, the at least one selected mm-wave FMCW radar sensor is configured to transmit signals towards a location of a subject's chest. In some implementations, the one or more proximity sensors comprise an array of capacitive proximity sensors positioned on a bed in the room. In some implementations, the multi-sensor system further includes a control system communicatively connected to the mm-wave FMCW radar sensor, the IMU sensor, and the one or more proximity sensors, where the control system is configured to: determine the body orientation of the subject using the one or more proximity sensors, select at least one of the one or more mm-wave FMCW radar sensors based on the body orientation, and adjust a view angle of the at least one selected mm-wave FMCW radar sensor to be directed towards a location of a subject's chest. In some implementations, the control system is further configured to: consolidate the first cardiovascular or respiratory measurement and the second cardiovascular or respiratory measurement to obtain an optimal cardiovascular or respiratory measurement.

Another innovative aspect of the subject matter described in this disclosure can be implemented in a method of calculating a consolidated cardiovascular or respiratory measurement using a multi-sensor system. The method includes identifying a presence of a subject in an interior of vehicle or room using one or more proximity sensors, determining a location of a subject's chest and/or body orientation of the subject using the one or more proximity sensors, adjusting a view angle of a mm-wave FMCW radar sensor positioned in the interior of the vehicle or room based on the location of the subject's chest and/or the body orientation of the subject, obtaining a first cardiovascular or respiratory measurement from the mm-wave FMCW radar sensor, obtaining a second cardiovascular or respiratory measurement from an IMU sensor, and consolidating the first and second cardiovascular or respiratory measurements to obtain an optimal cardiovascular or respiratory measurement.

In some implementations, the one or more proximity sensors comprise an array of capacitive proximity sensors positioned on a stationary object in the interior of the vehicle or room. In some implementations, the method further includes obtaining multiple cardiovascular or respiratory measurements from a plurality of mm-wave FMCW radar sensors in the vehicle or room for multiple subjects, each of the cardiovascular or respiratory measurements being calculated to determine a subject's stress level, level of drowsiness, or health. In some implementations, the method further includes selecting the mm-wave FMCW radar sensor from a plurality of mm-wave FMCW radar sensors based on the body orientation of the subject.

BRIEF DESCRIPTION OF THE DRAWINGS

Details of one or more implementations of the subject matter described in this specification are set forth in the accompanying drawings and the description below. Other features, aspects, and advantages will become apparent from the description, drawings and claims. Note that the relative dimensions of the following figures may not be drawn to scale.

Like reference numbers and designations in the various drawings indicate like elements.

DETAILED DESCRIPTION

The following description is directed to certain implementations for the purposes of describing various aspects of this disclosure. However, a person having ordinary skill in the art will readily recognize that the teachings herein can be applied in a multitude of different ways. Various embodiments will be described in detail with reference to the accompanying drawings. References made to particular examples and implementations are for illustrative purposes, and are not intended to limit the scope of the claims.

Contact-based or wired devices for monitoring vital signs may limit mobility and possibly spread contagious infections between patients and hospital staff. Contact-based connections may also add complexity and implementation difficulties where space is limited. Furthermore, contact-based connections may present challenges to individuals who may intentionally or accidentally detach the contact-based devices. Moreover, contact-based or wired connections may be burdensome or impractical to certain individuals such as burn patients. Contactless options may be valuable for heart and respiration rate monitoring, and can overcome the inconvenience and discomfort caused by wearing multiple wired electrodes and/or respiratory chest bands.

Radar sensors offer an alternative for non-invasive vital signs monitoring of humans. Traditionally, radar sensors have been used for speed measurements, gesture recognition, position estimation, people counting, imaging, and tumor detection, among other applications. Due to its property of electromagnetic backscattering, radar sensors can be used to wirelessly detect small displacements caused by human breathing and heart beats.

Millimeter-wave radar sensing is a contactless sensing technology that operates in a frequency domain between 30 GHz and 300 GHz and transmits signals with a wavelength in the millimeter range. Objects in the path reflect the signals back, and the millimeter-wave radar sensor is able to determine a range, velocity, and angle of the object(s). Millimeter-wave radar sensors can provide sub-millimeter precision for detecting small displacements, which make them ideal for sensing heart beats and breathing. Millimeter-wave radar signals are able to penetrate materials such as plastic, drywall, and clothing, and they are impervious to environmental conditions such as rain, fog, dust, and snow. A millimeter-wave sensor has characteristics of small size, lightweight, and high spatial resolution.

Various types of radar sensing can be employed for contactless vital signs monitoring. Continuous wave (CW) radar sensors emit a continuous wave radio frequency carrier and mix the transmitted radio frequency carrier with return echoes. This means that the return echo is received while transmitting. A Doppler shift provides the means to separate the transmitted signal from the received signal. Ultrawide band (UWB) radar sensors send a train of pulses towards a target and a received signal can be visualized in a frequency domain. Vital signs can be obtained in a time domain by analyzing time delay changes of a transmitted pulse. Frequency modulated continuous wave (FMCW) radar sensors send continuous modulated chirps. FMCW radar sensors are similar to CW radar sensors by sending continuous wave signals rather than transmitting short pulses periodically. In the case of FMCW radar sensors, however, the frequency increases linearly in the transmitted signal over a fixed period of time. This type of signal is called a "chirp." As the transmitted signal varies in frequency, the return signal has a different frequency. Range information of a target can be determined by the frequency difference between the return signal and the transmitted signal. The distance to the target is proportional to the frequency difference.

If the object moves towards or away from the FMCW radar sensor, the frequency and phase of the reflected chirp changes. When the wavelength is on the order of a few millimeters, a small change results in a large phase change so that it is easy to detect small movements. For example, a millimeter-wave FMCW radar sensor operating at 60 GHz or 77 GHz with a corresponding wavelength in the range of about 4 mm will have the ability detect movements that are as short as a fraction of a millimeter. As a result, micro-motions such as chest-wall movements caused by respiration or heart beats can be wirelessly detected.

Millimeter-wave FMCW radar sensing offers many advantages over UWB radar sensing. Millimeter-wave FMCW radar sensing has higher resolution, operates effectively at longer range distances, and provides better noise robustness. Though the electromagnetic signals in a millimeter-wave FMCW radar sensor is not able to penetrate the human body, it is very sensitive to small displacements of the human body including chest motions.

Figure 1A:
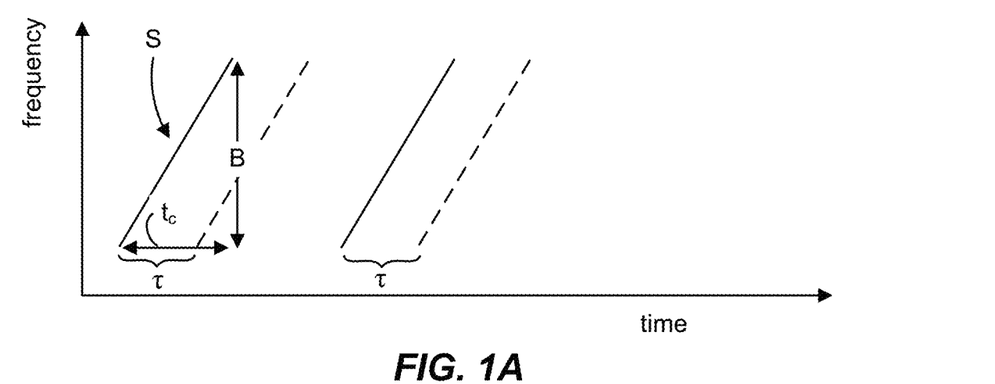
FIG. 1A shows a graph illustrating FMCW radar sensing of a stationary object with transmitted chirp signals and received signals.

FIG. 1A shows a graph illustrating FMCW radar sensing of a stationary object with transmitted chirp signals and received signals. An FMCW radar emits a chirp that is a continuous wave whose frequency is linearly modulated. When represented on a frequency versus time plot, a chirp that increases linearly with time is represented by a straight line having a certain slope. The chirp has a starting frequency and an ending frequency, and a difference between its starting frequency and ending frequency may be referred to as its bandwidth B. The bandwidth B and the time period $t_c$ may determine the slope S of the chirp, where the slope S defines the rate at which the chirp ramps up. The chirp is reflected off an object and received by an antenna. Assuming there is only one object in front of the radar, the received chirp is a time delay replica of the transmitted chirp. A round trip delay $\tau$ is proportional to the distance to the target object. When a subsequent chirp is transmitted and the reflected chirp results in the same round trip delay $\tau$, then the object in FIG. 1A is stationary.

Figure 1B:
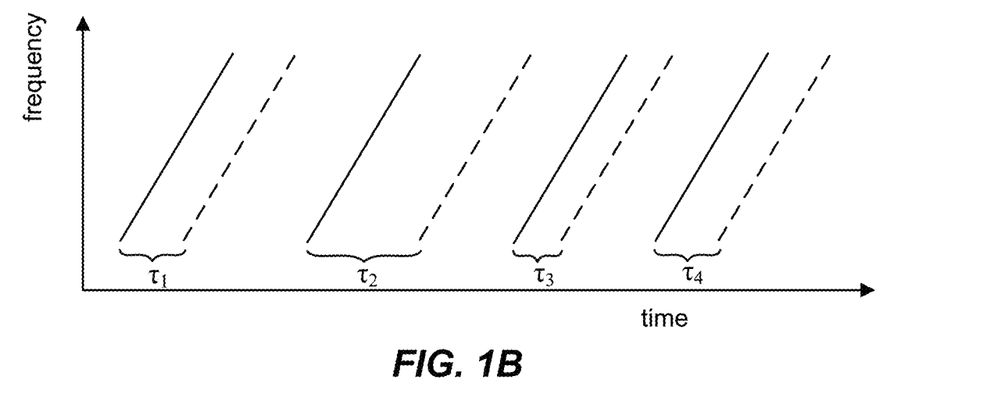
FIG. 1B shows a graph illustrating FMCW radar sensing of a non-stationary object with transmitted chirp signals and received signals.

FIG. 1B shows a graph illustrating FMCW radar sensing of a non-stationary object with transmitted chirp signals and received signals. Consecutive chirps are transmitted by the FMCW radar sensor. Each reflected chirp has a round trip delay $\tau_1$, $\tau_2$, $\tau_3$, and $\tau_4$. The round trip delay $\tau_1$ may be different than the round trip delay $\tau_2$, and the round trip delay $\tau_2$ may be different than the round trip delay $\tau_3$, and the round trip delay $\tau_3$ may be different than the round trip delay $\tau_4$. Furthermore, each of the reflected chirps may be varied in phase. Changes in round trip delay and phase show that the target object is changing position (i.e., moving) relative to the FMCW radar sensor. Vital signs can be obtained by an analysis of phase variations associated with a target position. For measuring vibrations such as heart beats or respiration, displacements of the object may be a fraction of a wavelength (e.g., a millimeter or less).

Figure 1C:
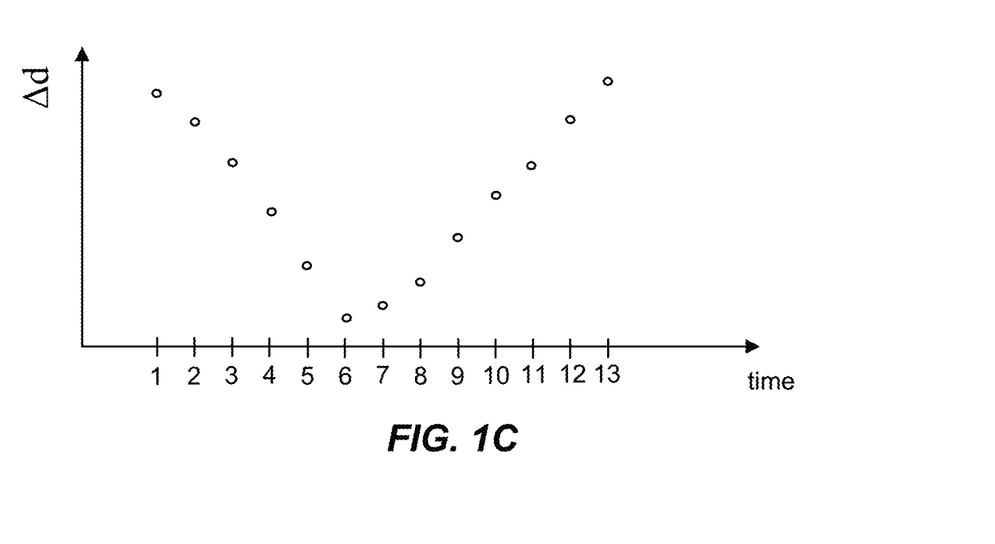
FIG. 1C shows a graph illustrating displacement as a function of time to measure heart rate using FMCW radar sensing.

FIG. 1C shows a graph illustrating displacement as a function of time to measure heart rate using FMCW radar sensing. Because the round trip delay $\tau$ can be correlated with displacement $\Delta d$, the displacements $\Delta d$ can be mapped on a plot showing displacement $\Delta d$ as a function of time. The displacement $\Delta d$ can be indicative of heartbeat or respiration. The displacements $\Delta d$ may occur as oscillatory motion.

There are many challenges associated with obtaining accurate cardiovascular and respiratory measurements using FMCW radar sensing technologies. Generally, an FMCW radar sensor having high directivity is better able to distinguish target objects from surrounding clutter. However, high directivity requires that a view angle of the FMCW radar sensor be pointed towards a person's chest for optimal performance. Moreover, a position and body orientation of a subject may enhance or compromise the performance of the FMCW radar sensor. For instance, a slight increase in measurement errors may occur if the subject's right side or back side is facing the FMCW radar sensor. The subject's setting and bodily motions may interfere with the performance of the FMCW radar sensor for obtaining accurate cardiovascular and respiratory measurements. Because the FMCW radar sensor may be highly sensitive motion artifacts, signals caused by various movements may be erroneously interpreted as heart beats or breathing. In one example, bumps or turbulence induced in a vehicle may cause bodily vibrations in a person that interfere with cardiovascular or respiratory measurements. In another example, a person on a bed may change position and/or orientation that can interfere with cardiovascular or respiratory measurements.

The present disclosure relates to a multi-sensor system for monitoring cardiovascular and respiratory data. The multi-sensor system includes a mm-wave FMCW radar sensor and one or more proximity sensors. The mm-wave FMCW radar sensor obtains a cardiovascular measurement such as a heart rate or a respiratory measurement such as a breathing rate. The one or more proximity sensors may detect the presence of the target subject. In some implementations, the one or more proximity sensors may detect the location of the target subject's chest so that the view angle of the mm-wave FMCW radar sensor can be adjusted to point towards the target subject's chest. In some implementations, the one or more proximity sensors may detect the body position and/or orientation of the target subject. The multi-sensor system may further include one or more inertial measurement unit (IMU) sensors. At least one of the IMU sensors may be used to obtain a cardiovascular or respiratory measurement. For example, the at least one IMU sensor may be used to obtain a ballistocardiogram for measuring heart rate. In some implementations, at least another one of the IMU sensors may be used to detect motion associated with the target subject's environment for filtering out noise in the target subject's cardiovascular or respiratory measurement.

Figure 2:
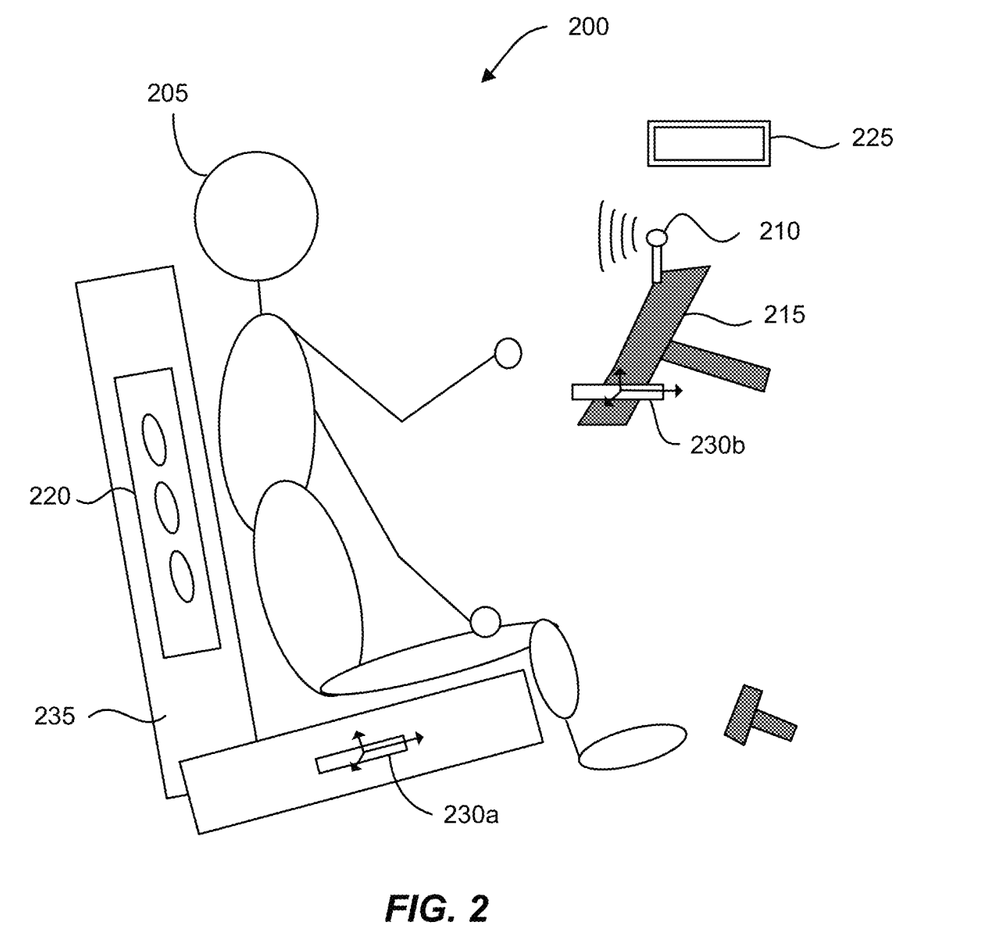
FIG. 2 shows a schematic illustration of a mm-wave FMCW radar sensor and one or more IMU sensors positioned in an interior of a vehicle according to some implementations.

FIG. 2 shows a schematic illustration of a mm-wave FMCW radar sensor and one or more IMU sensors positioned in an interior of a vehicle according to some implementations. Accordingly, a multi-sensor system 200 for monitoring cardiovascular or respiratory data may be implemented in a vehicle such as a car, bus, truck, train, aircraft, spacecraft, or watercraft. The multi-sensor system 200 includes a mm-wave FMCW radar sensor 210. The mm-wave FMCW radar sensor 210 may be positioned anywhere in the interior of the vehicle so that the mm-wave FMCW radar sensor 210 may be faced towards a subject 205. In some implementations, the mm-wave FMCW radar sensor 210 may be positioned on a steering wheel, dashboard, center console, overhead console, seat, top ceiling, rear-view mirror, or windshield. In one example, the mm-wave FMCW radar sensor 210 is positioned on the steering wheel 215. In another example, the mm-wave FMCW radar sensor 210 is positioned on the rear-view mirror 225.

The multi-sensor system 200 further includes one or more proximity sensors 220. The one or more proximity sensors 220 may be positioned anywhere in the interior of the vehicle so that the one or more proximity sensors 220 may detect the presence of the subject 205. In some implementations, the one or more proximity sensors 220 may be integrated in a seat 235 of a driver or passenger. Specifically, the one or more proximity sensors 220 may be positioned inside the seat 235, positioned on an outer surface of the seat 235, or positioned underneath the seat 235. In some implementations, the one or more proximity sensors 220 may include an array of capacitive proximity sensors. It will be understood that the one or more proximity sensors 220 may include other types of proximity sensors known in the art.

The multi-sensor system 200 further includes one or more IMU sensors 230a, 230b. A first IMU sensor 230a may be positioned anywhere in the interior of the vehicle to acquire motion data associated with the subject 205. The first IMU sensor 230a may be a motion sensor such as an accelerometer positioned to acquire cardiovascular or respiratory data associated with the subject 205. In some cases, the first IMU sensor 230a can acquire a ballistocardiogram of the subject 205. In some implementations, the first IMU sensor 230a may be positioned inside the seat 235, positioned on an outer surface of the seat 235, or positioned underneath the seat 235. A second IMU sensor 230b may be positioned anywhere in the interior of the vehicle to acquire motion data associated with the vehicle. Such motion data may relate to internal motion activity occurring in the interior of the vehicle. In particular, sudden bumps, dips, turns, jerks, stops, acceleration, deceleration, and other motions of the vehicle may cause components in the interior of the vehicle to move or vibrate. This may cause the subject 205 in the interior of the vehicle to move or vibrate, which can interfere with the monitoring of cardiovascular or respiratory data of the subject 205. The second IMU sensor 230b may register such motions occurring in the vehicle to account for "noise" or "motion artifacts" in the cardiovascular or respiratory data acquired from the first IMU sensor 230a or the mm-wave FMCW radar sensor 210. In some implementations, the second IMU sensor 230b may be positioned on the steering wheel, dashboard, center console, overhead console, seat, top ceiling, rear-view mirror, or windshield of the vehicle. For instance, the second IMU sensor 230b is positioned on the steering wheel 215.

In some implementations, the one or more proximity sensors 220 may be configured to estimate a location of the subject's chest. As used herein, the location of the subject's chest may also refer to a height of the subject's chest. The location of the subject's chest may be determined relative to the location of the mm-wave FMCW radar sensor 210. In some implementations, the one or more proximity sensors 220 may acquire a map, contour, or outline of the subject's body in the vehicle. Specifically, the one or more proximity sensors 220 may acquire a map, contour, or outline of at least the subject's torso. Using the outline of the subject's body or torso, the one or more proximity sensors 220 can calculate a height of the subject's chest.

Once the location of the subject's chest is determined relative to the location of the mm-wave FMCW radar sensor 210, a view angle of the mm-wave FMCW radar sensor 210 can be adjusted to be directed towards the location of the subject's chest. That way, transmitted signals from the mm-wave FMCW radar sensor 210 can be better focused towards the region of interest. This more effectively isolates reflected signals corresponding to heart beats and respiration from other motions/vibrations. The mm-wave FMCW radar sensor 210 may be pointed to the subject's chest so that the subject's chest is in the line-of-sight of the mm-wave FMCW radar sensor 210. Because the mm-wave FMCW radar sensor 210 may emit signals with high directivity, strongest signals are emitted within the radar sensor's view angle while weaker signals are emitted outside the view angle. A view angle represents a radiation pattern of the radio-frequency signals. Generally, the mm-wave FMCW radar sensor 210 generates signals with a viewing area so that motions/vibrations are effectively isolated within the viewing area. For example, the viewing area may be within about 10 degrees, within about 20 degrees, within about 30 degrees, within about 40 degrees, or within about 45 degrees of the radar sensor's view angle. Many mm-wave FMCW radar sensors capture 20 degrees to 30 degrees cone to the front of an antenna. Right at the middle (i.e., 0 degrees) gives the strongest signal with the optimal signal-to-noise ratio. Some attenuation of the signal may occur when deviating from the middle. Nonetheless, the subject's chest may be within the viewing area of the mm-wave FMCW radar sensor 210 even if the view angle is not perfectly aligned with the subject's chest. Pointing the mm-wave FMCW radar sensor 210 in the direction of the subject's chest allows the measurement to be optimally correlated with heart beat or respiration.

Figure 4A:
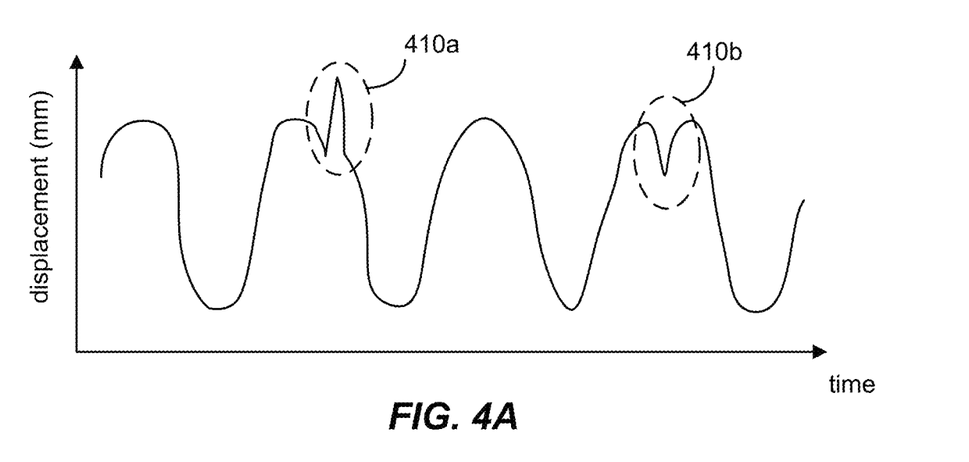
FIG. 4A shows a graph illustrating an example cardiovascular measurement obtained from a mm-wave FMCW radar sensor.
Figure 4B:
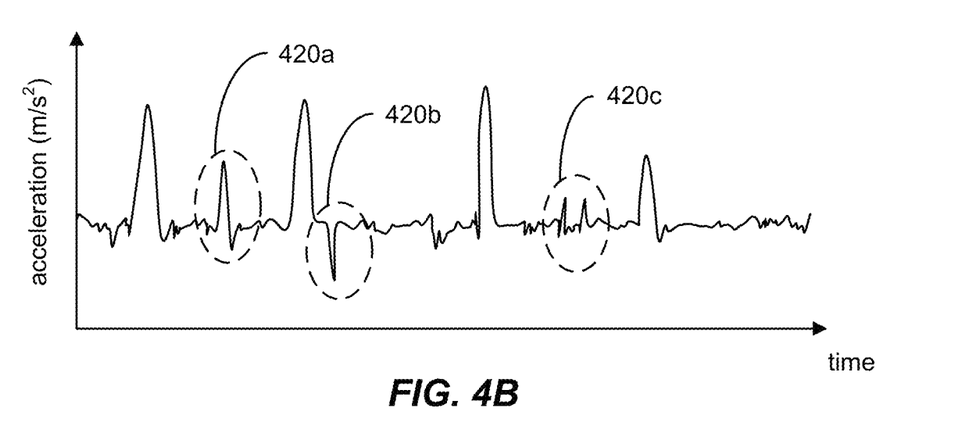
FIG. 4B shows an example ballistocardiogram capturing a heartbeat pattern obtained from an IMU sensor.

The mm-wave FMCW radar sensor 210 may acquire a cardiovascular measurement such as a heartbeat or a respiratory measurement such as a breathing rate. Acquisition of the cardiovascular or respiratory measurement can occur after the view angle is adjusted to be directed towards the subject's chest. An example cardiovascular measurement acquired from the mm-wave FMCW radar sensor 210 is shown in FIG. 4A. The first IMU sensor 230a may also acquire a cardiovascular measurement such as a heartbeat or a respiratory measurement such as a breathing rate. For instance, the first IMU sensor 230a may acquire a ballistocardiogram that records a heartbeat pattern. An example ballistocardiogram is shown in FIG. 4B. Data from the mm-wave FMCW radar sensor 210 and the first IMU sensor 230a may be fused for improved accuracy.

The first IMU sensor 230a may serve as a ballistocardiograph (BCG) system that can be integrated in seats, beds, and other everyday objects to record cardiac activity of the subject 205. In FIG. 2, the first IMU sensor 230a may be integrated in the seat 235 and record cardiac activity of the subject 205 while the subject 205 is seated. The first IMU sensor 230a is sensitive enough to detect vibrations of the body caused by mechanical activity of the heart.

The data from the mm-wave FMCW radar sensor 210 may be represented as a first cardiovascular or respiratory measurement, and the data from the first IMU sensor 230a may be represented as a second cardiovascular or respiratory measurement. The first cardiovascular or respiratory measurement and the second cardiovascular or respiratory measurement may be consolidated. How aggressive the signals are filtered out in a cardiovascular or respiratory measurement may depend on a calculated confidence factor associated with the measurement technique. In some implementations, the associated confidence factor may be based on various factors affecting the accuracy of the measurement technique, including but not limited to: an amount of noise in the cardiovascular or respiratory measurement, relative difference between the cardiovascular or respiratory measurements, a position or body orientation of the subject 205, location of the mm-wave FMCW radar sensor 210 relative to the subject's chest, location of the first IMU sensor 230a relative to the subject 205, periodicity of signals in the cardiovascular or respiratory measurement, and sensitivity of the mm-wave FMCW radar sensor 210 and first IMU sensor 230a, among other factors. The confidence factor may be estimated by a probabilistic model for the received signal or measurement. A matched filter output can give an indication about a target with signal strength directly linked to a likelihood function used in statistical hypothesis testing through the Karhunen-Loève transform, giving a confidence factor related to the cardiovascular or respiratory measurement. From there, the confidence factor is further estimated based on whether the cardiovascular or respiratory measurement captures the actual heart beat or respiration of the subject 205. This can be done using another probabilistic modeling using temporal statistical assumptions. Data fusion of the first and second cardiovascular or respiratory measurements may proceed according to the estimated confidence factors. In some implementations, the measurement with the higher confidence factor is chosen. Specifically, the first cardiovascular or respiratory measurement may be selected if the confidence factor of the first cardiovascular or respiratory measurement is more than the second cardiovascular or respiratory measurement, or the second cardiovascular or respiratory measurement may be selected if the confidence factor of the second cardiovascular or respiratory measurement is more than the first cardiovascular or respiratory measurement. In some implementations, the first and second cardiovascular or respiratory measurements are combined in a Bayesian fashion that models the measurement uncertainty by computing a posterior distribution, in contrast to accepting or rejecting a single point estimate. The confidence factor of a measurement technique may change over time as the context in the environment changes. The confidence factors associated with different measurement techniques may change over time as the relative accuracy of the measurement techniques change over time. This can occur as the setting changes and/or the subject 205 moves around.

Consolidation of the first and second cardiovascular or respiratory measurements combine data streams to provide an optimal cardiovascular or respiratory measurement. The optimal cardiovascular or respiratory measurement may be a heartbeat pattern or breathing rate pattern represented as a single data stream for improved accuracy and reliability.

Figure 4C:
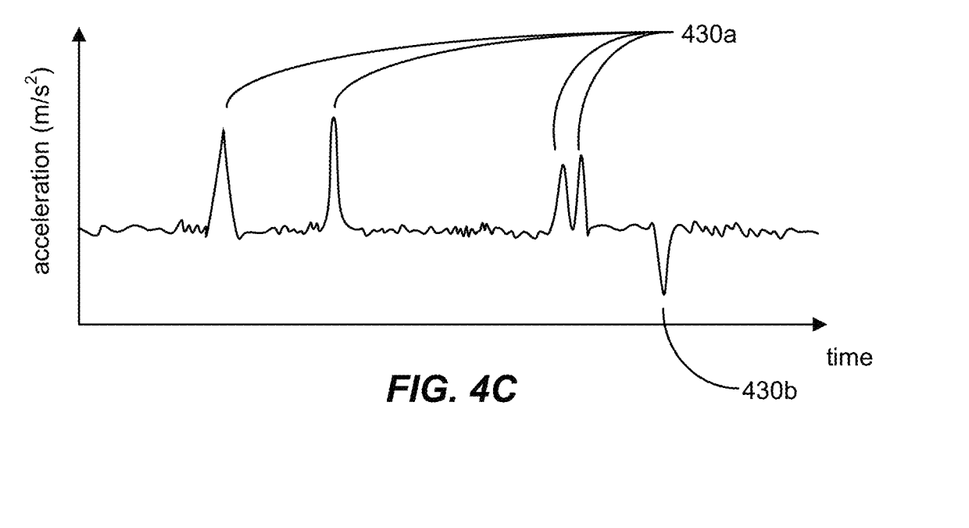
FIG. 4C shows a graph illustrating motion activity from a moving vehicle obtained from an IMU sensor.

In some implementations, the motion data associated with the vehicle acquired from the second IMU sensor 230b may be consolidated with the first cardiovascular or respiratory measurement and/or the second cardiovascular or respiratory measurement. Various motion artifacts caused by the vehicle may interfere with an accurate cardiovascular or respiratory measurement. Such motion artifacts caused by the vehicle may appear as heart beats or respiration in a cardiovascular or respiratory measurement. Motion artifacts may appear as spikes or anomalies in a data stream. An example data stream for detecting motion artifacts caused by the vehicle is shown in FIG. 4C.

The second IMU sensor 230b may record such motion artifacts so that any motion artifacts caused by the vehicle can be subtracted from the first cardiovascular or respiratory measurement and/or the second cardiovascular or respiratory measurement. A denoised first cardiovascular or respiratory measurement can be obtained by calculating the relative difference between the first cardiovascular or respiratory measurement and the motion data associated with the vehicle. Alternatively, a denoised first cardiovascular or respiratory measurement can be obtained by calculating the relative difference between the second cardiovascular or respiratory measurement and the motion data associated with the vehicle. Or, a denoised optimal cardiovascular or respiratory measurement can be obtained by calculating the relative difference between the optimal cardiovascular or respiratory measurement and the motion data associated with the vehicle Eliminating bodily motion artifacts from the optimal (fused) cardiovascular or respiratory measurement improves accuracy and reliability.

As shown in FIG. 2, the one or more proximity sensors 220 may serve to detect driver/passenger presence in the vehicle and determine a height or location of a subject's chest. This information may be used to optimize a view angle of the mm-wave FMCW radar sensor 210 for improved accuracy and performance in obtaining cardiovascular or respiratory measurements. Additionally, the first IMU sensor 230a and the second IMU sensor 230b supplement, reinforce, adjust, or improve data gathered by the mm-wave FMCW radar sensor 210. The first IMU sensor 230a may acquire motion data associated with the subject's body to be consolidated with the cardiovascular or respiratory measurement acquired from the mm-wave FMCW radar sensor 210. Such motion data may be related to heart rate or respiration rate. Or, such motion data may be used to denoise bodily motion artifacts. The second IMU sensor 230b may acquire motion data associated with the vehicle. Such motion data may be used to denoise motion artifacts that may appear in cardiovascular or respiratory measurements.

The denoised optimal cardiovascular or respiratory measurement can be analyzed to ascertain information about the subject 205. In some implementations, the denoised optimal cardiovascular or respiratory measurement can be leveraged to determine different metrics such as stress level, level of drowsiness, or health level of the subject 205. By way of an example, after a heart rate or respiration rate is measured, a drowsiness level of the driver or passenger in a vehicle can be determined using the heart rate or respiration rate. If the drowsiness level meets a certain threshold, predefined actions may be performed. Such predefined actions may include but are not limited to: immediate audio alerts, immediate light alerts, immediate phone alert, immediate video alert, engine/braking control, contact remote operator, etc. These actions serve the goal of trying to wake up the driver or passenger. In some implementations, multiple setups of mm-wave FMCW radar sensors 210, proximity sensors 220, first IMU sensors 230a, and second IMU sensors 230b may be arranged in the vehicle for obtaining cardiovascular or respiratory measurements of multiple occupants. The measured heart rate or respiration rate can be leveraged to determine a stress level, level of drowsiness, or health of each of the passengers. For instance, depending on the level of drowsiness of the passengers, an audio system of the vehicle may be adjusted in volume if one or more passengers are asleep. Alternatively, depending on the level of drowsiness of the passengers, a temperature of an air conditioning system in the vehicle may be adjusted.

Figure 3:
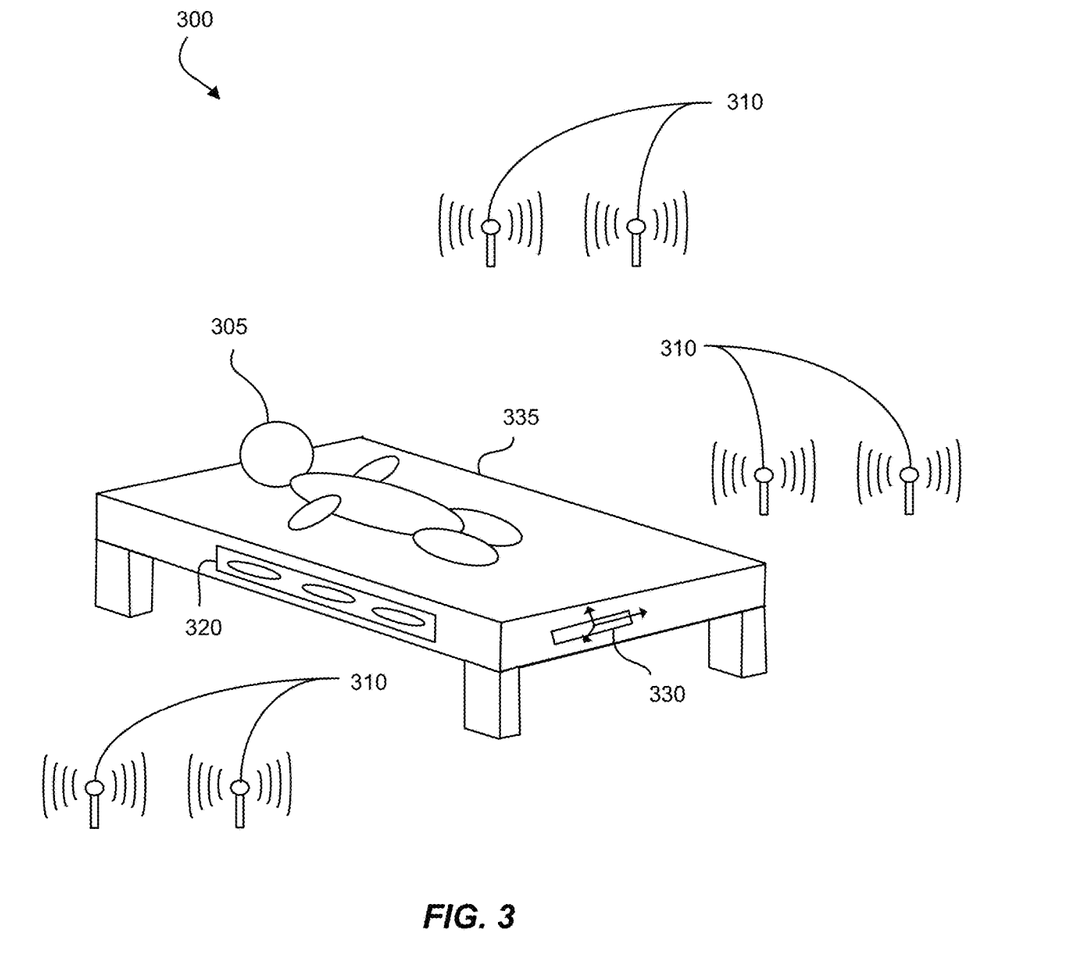
FIG. 3 shows a schematic illustration of one or more mm-wave FMCW radar sensors and an IMU sensor positioned in a room according to some implementations.

FIG. 3 shows a schematic illustration of one or more mm-wave FMCW radar sensors and an IMU sensor positioned in a room according to some implementations. A multi-sensor system 300 for monitoring cardiovascular or respiratory data may be implemented in a room with a subject 305. The room may be any space in which the subject 305 may be situated for a relatively long duration so that continuous tracking of cardiovascular or respiratory data can occur. In some implementations, the room may be a hospital room, a bedroom, a library room, an office space, or other space where the subject 305 may be lying down, sitting, or relatively stationary for long periods. For instance, the room may be a hospital room.

The multi-sensor system 300 for monitoring cardiovascular or respiratory data may include one or more mm-wave FMCW radar sensors 310. In some implementations, a plurality of mm-wave FMCW radar sensors 310 may be positioned in different locations of the room. Each of the mm-wave FMCW radar sensors 310 may be positioned in the room to be faced towards the subject 305. Or, each of the mm-wave FMCW radar sensors 310 may be positioned in the room to at least be facing towards a stationary object such as a bed or chair that the subject 305 would be located on. In some implementations, the mm-wave FMCW radar sensors 310 are positioned on walls, ceilings, or stationary objects around the room.

The multi-sensor system 300 further includes one or more proximity sensors 320. The one or more proximity sensors 320 may be positioned anywhere in the room to detect the presence of the subject 305. Furthermore, the one or more proximity sensors 320 may be positioned anywhere in the room to determine a body orientation and/or position of the subject 305 in the room. In some implementations, the one or more proximity sensors 320 are integrated in a bed 335 in the room. For example, the one or more proximity sensors 320 may be positioned inside the bed 335, positioned on an outer surface of the bed 335, or positioned underneath the bed 335. It will be understood that the one or more proximity sensors 320 may be integrated in any stationary object where the subject 305 may be located on or in proximity to. Other stationary objects may include but are not limited to chairs, couches, pillows, mats, tables, desks, and the like. In some implementations, the one or more proximity sensors 320 may include an array of capacitive proximity sensors. In some implementations, the one or more proximity sensors 320 may include a time-of-flight sensor. In some implementations, the one or more proximity sensors 320 may include an optical sensor (camera). In some implementations, the one or more proximity sensors 320 may include one or more pressure transducers. It will be understood that the one or more proximity sensors may include other types of proximity sensors known in the art.

The multi-sensor system 300 further includes an IMU sensor 330. An IMU sensor 330 may be positioned anywhere in the room to acquire motion data associated with the subject 305. The IMU sensor 330 may be a motion sensor positioned to acquire cardiovascular or respiratory data associated with the subject 330. In some cases, the IMU sensor 330 can acquire a ballistocardiogram of the subject 305. In some implementations, the IMU sensor 330 may be positioned inside the bed 335, positioned on an outer surface of the bed 3335, or positioned underneath the bed 335. In some implementations, both the IMU sensor 330 and the one or more proximity sensors 320 may be positioned in the same location, e.g., underneath the bed 335. Strong signals registered by the IMU sensor 330 may be indicative of bodily motions unrelated to heartbeat or respiration patterns, and may be used for denoising cardiovascular or respiratory measurements acquired from the one or more mm-wave FMCW radar sensors 310. Prior knowledge or information of how much acceleration a human body typically produces due to blood flow or respiration can establish a threshold acceleration value, and acceleration values that are much higher (e.g., at least two times greater) than the threshold acceleration value can be indicative of bodily motions unrelated to heartbeat or respiration patterns. Weak signals registered by the IMU sensor 330 may be indicative of heartbeat or respiration patterns, and may be consolidated with cardiovascular or respiratory measurements acquired from the one or more mm-wave FMCW radar sensors 310.

In some implementations, the one or more proximity sensors 320 may be configured to estimate a body orientation of the subject 305. The body orientation of the subject 305 may refer to a direction in three-dimensional (3-D) space that the frontal plane (anterior) of the body is facing. The body orientation may be relative to an object in the room such as the bed 335 or one of the mm-wave FMCW radar sensors 310. Accordingly, the one or more proximity sensors 320 may determine if the subject 305 is facing forward, facing back, facing sideways left, facing sideways right, lying prone, lying supine, lying sideways left, or lying sideways right. In some implementations, the one or more proximity sensors 320 may acquire a map, contour, or outline of the subject's body or at least the subject's torso. In some implementations, the one or more proximity sensors 320 may acquire a location (e.g., height) of the subject's chest relative to the bed 335.

Once the body orientation of the subject 305 is determined relative to the room, at least one of the one or more mm-wave FMCW radar sensors 310 may be selected for obtaining a cardiovascular or respiratory measurement of the subject 305. When multiple mm-wave FMCW radar sensors 310 are positioned in different locations of the room, only some of the mm-wave FMCW radar sensors 310 are positioned to be directed towards the subject's frontal plane. At least one mm-wave FMCW radar sensor 310 is selected so that subject's frontal plane is in the line-of-sight with the at least one of the mm-wave FMCW radar sensor 310. Utilizing the mm-wave FMCW radar sensor 310 that faces the frontal plane of the subject 305 improves the accuracy of cardiovascular or respiratory measurements. Front-side measurements provide the most accurate measurements, left-side measurements provide a relatively high degree of accuracy and are slightly less accurate than front-side measurements, back-side measurements provide slightly less accurate measurements than left-side measurements, and right-side measurements provide the least accurate measurements. The at least one mm-wave FMCW radar sensor 310 may be selected that faces the subject's body orientation providing the most accurate measurements.

In some implementations, the multi-sensor system 300 may be limited to a single mm-wave FMCW radar sensor 310 in the room. The single mm-wave FMCW radar sensor 310 may not be directed towards the subject's frontal plane. In such cases, a confidence factor (e.g., error rate, success rate) may be calculated to ascertain how accurate the cardiovascular or respiratory measurement is for the single mm-wave FMCW radar sensor 310. The confidence factor depends on the body orientation of the subject 305 with respect to the single mm-wave FMCW radar sensor 310. The confidence factor may account for errors that may arise when obtaining cardiovascular or respiratory measurements when the subject's frontal plane is not in line-of-sight with the mm-wave FMCW radar sensor 310. Or, in some instances where there are a plurality of mm-wave FMCW radar sensors 310 in the room, none of the mm-wave FMCW radar sensors 310 may be directed towards the subject's frontal plane. In such cases, a confidence factor may be calculated for each of the mm-wave FMCW radar sensors 310, and the mm-wave FMCW radar sensor 310 with the highest confidence factor may be selected.

In some implementations, a view angle of the at least one mm-wave FMCW radar sensor 310 is adjusted to be directed towards the location of the subject's chest. This may occur after obtaining a location of the subject's chest using the one or more proximity sensors 320. The mm-wave FMCW radar sensor 310 may be pointed to the subject's chest so that the subject's chest is in the line-of-sight of the at least one mm-wave FMCW radar sensor 310. Adjusting the view angle of the at least one mm-wave FMCW radar sensor to be directed towards the subject's chest optimizes the accuracy of cardiovascular or respiratory measurements obtained by the at least one mm-wave FMCW radar sensor 310. The at least one mm-wave FMCW radar sensor 310 may emit signals with a viewing area so that motions/vibrations are effectively isolated within the viewing area. For instance, the viewing area may be within 10 degrees, within about 20 degrees, within about 30 degrees, within about 40 degrees, or within about 45 degrees of the radar sensor's view angle. Therefore, the subject's chest may be within the viewing area of the mm-wave FMCW radar sensor 310 even if the view angle is not perfectly aligned with the subject's chest.

The at least one mm-wave FMCW radar sensor 310 may acquire a cardiovascular measurement such as a heartbeat or a respiratory measurement such as a breathing rate. Acquisition of the cardiovascular or respiratory measurement may occur after the view angle is adjusted to be directed towards the subject's chest. The IMU sensor 330 may also acquire a cardiovascular measurement such as a heartbeat or a respiratory measurement such as a breathing rate. For instance, the IMU sensor 330 may acquire a ballistocardiogram that records a heartbeat pattern. In FIG. 3, the IMU sensor 330 may be integrated in the bed 335 and record cardiac activity while the subject 305 is on the bed 335. The IMU sensor 330 is sensitive enough to detect vibrations of the body caused by mechanical activity of the heart. Data from the at least one mm-wave FMCW radar sensor 310 and the IMU sensor 330 may be fused for improved accuracy.

The data from the at least one mm-wave FMCW radar sensor 310 may be represented as a first cardiovascular or respiratory measurement, and the data from the IMU sensor 330 may be represented as a second cardiovascular or respiratory measurement. The first cardiovascular or respiratory measurement and the second cardiovascular or respiratory measurement may be consolidated. Consolidation techniques for fusing the first and second cardiovascular or respiratory measurements are described above in FIG. 2. The first cardiovascular or respiratory measurement may have an associated confidence factor, and the second cardiovascular or respiratory measurement may have an associated confidence factor. Each confidence factor is based at least in part on the body orientation of the person and/or a difference between the first cardiovascular or respiratory measurement and the second cardiovascular or respiratory measurement. Thus, the confidence factor for a measurement technique may depend on if the subject 305 is sitting, lying prone, lying supine, lying sideways left, or lying sideways right. For example, a lower confidence factor may be estimated according to how the subject 305 faces the mm-wave FMCW radar sensor 310 or how proximate the subject 305 is to the IMU sensor 330. The first and second cardiovascular or respiratory measurements are consolidated according to an algorithm based in part on the first and second associated confidence factors to obtain the optimal cardiovascular or respiratory measurement.

Consolidation of the first and second cardiovascular or respiratory measurements combine data streams to provide an optimal cardiovascular or respiratory measurement. Consolidation of the first and second cardiovascular or respiratory measurements may undergo an adaptive filtering process. Filter parameters change depending on the inputs of the IMU sensor 330 and/or inputs of the mm-wave FMCW radar sensor 310. In adaptive filtering, a heartbeat or respiratory cycle typically evolves smoothly over time. A smoothness constraint for a heartbeat or respiratory state variable can be applied during an estimation process. The adaptive filtering process only permits cardiovascular or respiratory measurements that satisfy the smoothness constraint in order to be considered a heartbeat or respiration. Otherwise, the cardiovascular or respiratory measurement is cancelled or removed. This is an adaptive process over time conditioned on current heart rate or respiration rate states.

The second cardiovascular or respiratory measurement provided from the IMU sensor 330 may assist in fusing or filtering data. As discussed above, weak vibration signals observed by the IMU sensor 330 may qualify as cardiovascular or respiratory measurements, and strong motion signals observed by the IMU sensor 330 may qualify as motion artifacts for denoising. Strong motion signals may appear as spikes that are at least twice in amplitude compared to weak vibration signals. The strong motion signals recorded by the IMU sensor 330 may be subtracted from the first cardiovascular or respiratory measurement provided from the mm-wave FMCW radar sensor 310. The weak vibration signals recorded by the IMU sensor 330 may be added to the first cardiovascular or respiratory measurement provided from the mm-wave FMCW radar sensor 310 where the mm-wave FMCW radar sensor 310 does not record a heartbeat pattern or breathing pattern. Alternatively, the weak vibration signals recorded by the IMU sensor 330 may be added to the first cardiovascular or respiratory measurement provided from the mm-wave FMCW radar sensor 310 where the confidence factor associated with the mm-wave FMCW radar sensor 310 is low.

As shown in FIG. 3, the one or more proximity sensors 320 may serve to detect a subject's presence in a room and determine a body orientation of the subject 305. In some implementations, the one or more proximity sensors 320 further determine a height or location of the subject's chest. This information may be used to optimize a view angle of the one or more mm-wave FMCW radar sensors 310 for improved accuracy and performance in obtaining cardiovascular or respiratory measurements. Furthermore, the IMU sensor 330 may acquire motion data associated with the subject's body. The motion data may be related to the heart rate or respiration rate in some time periods, or the motion data may be related to bodily motion artifacts in other time periods. The motion data associated with the subject's body may be consolidated with the cardiovascular or respiratory measurement acquired from the one or more mm-wave FMCW radar sensors 310. In some instances or time periods, the motion data associated with the subject's body may be added to, subtracted from, averaged with, or otherwise consolidated with the cardiovascular or respiratory measurement acquired from the one or more mm-wave FMCW radar sensors 310. How the measurements are consolidated can depend on factors such as confidence factors associated with the measurement technique, body orientation of the subject 305, etc. The foregoing consolidation provides a denoised optimal cardiovascular or respiratory measurement.

The denoised optimal cardiovascular or respiratory measurement can be analyzed to ascertain information about the subject 305. In some implementations, the denoised optimal cardiovascular or respiratory measurement can be leveraged to monitor vital signs or other health metrics of the subject 305. By way of an example, a heart rate or respiration rate of a patient in a hospital bed can be monitored. If the heart rate or respiration rate reaches below a threshold level, then an alert can be triggered to a doctor or other healthcare worker. In another example, heart rate variability can be estimated from the denoised optimal cardiovascular measurement, which can be used to correlate with many chronic diseases. It can also be used to correlate with stress level or anxiety. In still another example, respiration measurements can be used to detect speech that can be analyzed to correlate with a subject's neural system health.

FIG. 4A shows a graph illustrating an example cardiovascular measurement obtained from a mm-wave FMCW radar sensor. The cardiovascular measurement may be a subject's heart rate. A mm-wave FMCW radar sensor can detect vibrations or small changes in displacement over time. The small changes in displacement can be correlated with round trip delay when transmitting chirps. The small changes in displacement can be visually represented on the graph shown in FIG. 4A as oscillatory motion. Interferences 410a, 410b may appear on the graph that interrupt the oscillatory motion. The interferences 410a, 410b may be caused by bodily motion artifacts unrelated to a subject's heartbeat or respiration.

FIG. 4B shows an example ballistocardiogram capturing a heartbeat pattern obtained from an IMU sensor. The ballistocardiogram may graphically represent repetitive motions of the body arising from sudden ejection of blood from a subject's blood vessels. The ballistocardiogram may be obtained from an IMU such as an accelerometer. Vibrations from the subject's body may be transferred to another object (e.g., chair, bed, weight scale) and recorded by the accelerometer to record heart activity. Interferences 420a, 420b, 420c may appear on the ballistocardiogram as "noise." In some cases, this noise may be a result of motion induced on the object to which the accelerometer is attached, where such motion is unrelated to the subject's heartbeat or respiration. One or more of the interferences 420a, 420b, 420c in FIG. 4B may be correlated with the interferences 410a, 410b in FIG. 4A.

FIG. 4C shows a graph illustrating motion activity from a moving vehicle obtained from an IMU sensor. The IMU sensor may be an accelerometer that is attached to an object in the vehicle. Motion activity (e.g., vibrations) induced on the object in the vehicle may give rise to signals 430a, 430b. These signals 430a, 430b correspond to motions unrelated to a subject's heartbeat or respiration. These signals 430a, 430b may be caused by, for example, sudden motions in the vehicle such as bumps, dips, or turns. These signals 430a, 430b may be correlated with interferences 410a, 410b for denoising the cardiovascular measurement in FIG. 4A, or correlated with interferences 420a, 420b, 420c for denoising the ballistocardiogram in FIG. 4B.

Figure 4D:
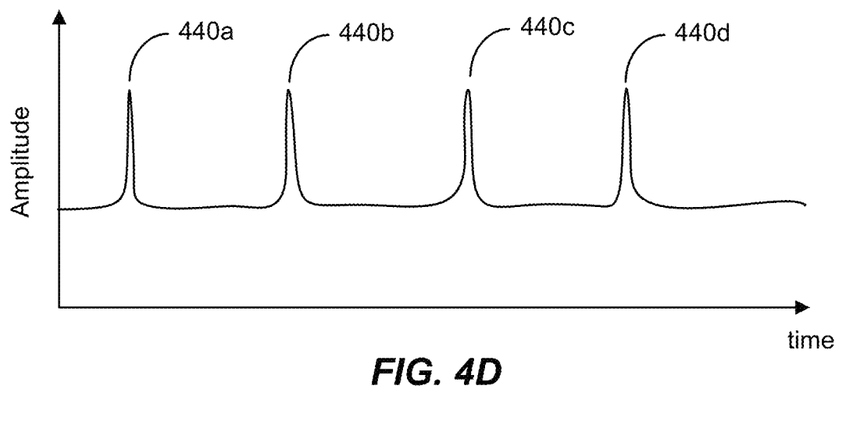
FIG. 4D shows a graph illustrating an optimized cardiovascular measurement obtained by consolidating data from multiple sensors according to some implementations.

FIG. 4D shows a graph illustrating an optimized cardiovascular measurement obtained by consolidating data from multiple sensors according to some implementations. The optimized cardiovascular measurement may record a heartbeat pattern that is denoised of motion artifacts using one or both of IMU sensor data in FIGS. 4B and 4C. The optimized cardiovascular measurement may eliminate interferences 410a, 410b in FIG. 4A and interferences 420a, 420b, 420c in FIG. 4B, and fuse heartbeat data from FIGS. 4A and 4B for a more accurate and reliable heartbeat pattern. The optimized cardiovascular measurement may record heart beats 440a, 440b, 440c, 440d by consolidating measurements from FIGS. 4A-4C.

Figure 5:
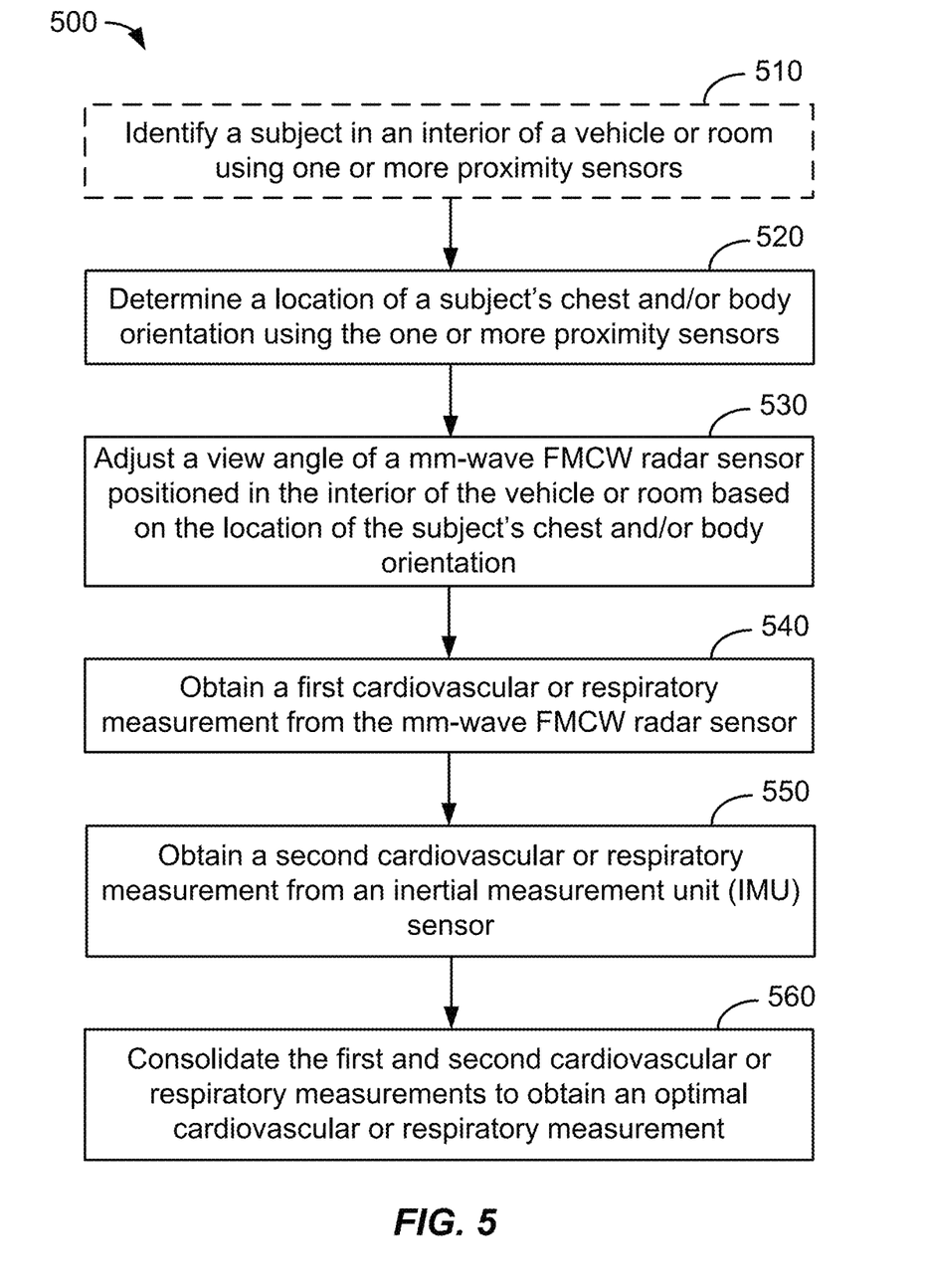
FIG. 5 shows a flow diagram illustrating an example process for calculating a consolidated cardiovascular or respiratory measurement using a multi-sensor system according to some implementations.

FIG. 5 shows a flow diagram illustrating an example process for calculating a consolidated cardiovascular or respiratory measurement using a multi-sensor system according to some implementations. A process 500 may be performed in a different order or with different, fewer, or additional operations. The blocks of the process 500 may be performed by one or more processors of a control system. In some implementations, the blocks of the process 500 may be implemented, at least in part, according to software stored on one or more non-transitory computer readable media.

At block 510 of the process 500, a subject is optionally identified in an interior of a vehicle or room using one or more proximity sensors. The one or more proximity sensors may include an array of capacitive proximity sensors. Or, the one or more proximity sensors may include other types of sensors such as optical, photoelectric, time-of-flight, and pressure sensors. Such proximity sensors may be leveraged to determine if a subject is inside the vehicle or room. The identified subject may be any mammalian subject such as a human person. In some implementations, the one or more proximity sensors may determine that the subject is stationary or substantially stationary for a sufficient duration at a certain location in the vehicle or room. A sufficient duration may be on the order of seconds or minutes, such as about 3 seconds, 5 seconds, 10 seconds, 30 seconds, 1 minute, 2 minutes, or 3 minutes. That way, a cardiovascular or respiratory measurement may be initiated when it is determined that the subject is not going in and out of the vehicle or room. In some implementations, the vehicle can include a car, bus, truck, train, aircraft, spacecraft, or watercraft. In some implementations, the room can include a hospital room, a bedroom, a library room, an office space, or other enclosed space where the subject may be relatively stationary for long periods of time.

A multi-sensor system of the present disclosure may include the one or more proximity sensors and a control system. The control system may include a processor and/or memory. The processor may be programmed with processor-executable instructions. The processor may be a programmable microprocessor, microcomputer, or multiple processor chip(s) that can be configured by software instructions to perform a variety of functions associated with the multi-sensor system. The memory may store processor-executable instructions as well as data obtained from the one or more proximity sensors and other sensors. In some implementations, the memory may be a volatile memory, non-volatile memory (e.g., flash memory), or a combination thereof. The control system may be in electrical communication (directly or indirectly) with the one or more proximity sensors and other sensors. The control system may receive data (e.g., raw data) from the one or more proximity sensors and other sensors. The control system may include dedicated hardware specifically adapted to perform a variety of functions for the multi-sensor system.

At block 520 of the process 500, a location of the subject's chest and/or body orientation is determined using the one or more proximity sensors. In addition or in the alternative to detecting the presence of the subject, the one or more proximity sensors may detect how the subject is positioned relative to the vehicle or room. Ascertaining how the subject is positioned relative to the vehicle or room will assist other sensors in acquiring accurate cardiovascular or respiratory measurements. In some implementations, the one or more proximity sensors may acquire a map, outline, or contour of the subject's body. Leveraging such information, the one or more proximity sensors may determine the location of the subject's chest relative to other sensors in the vehicle or room. In some implementations, the one or more proximity sensors may determine the body orientation of the subject relative to other sensors in the vehicle or room. Possible body orientations may include facing forward, facing back, facing sideways left, facing sideways right, lying prone, lying supine, lying sideways left, or lying sideways right.

The other sensors in the room may include one or more mm-wave FMCW radar sensors or one or more IMU sensors.

The control system may receive positioning data from the one or more proximity sensors, where the control system may identify the presence of the subject in the vehicle or room using the positioning data, and where the control system may determine a location of the subject's chest and/or body orientation of the subject using the positioning data. In some implementations, the control system may use the positioning data to determine the location of the subject's chest relative to a mm-wave FMCW radar sensor. In some implementations, the control system may use the positioning data to determine the body orientation of the subject relative to the mm-wave FMCW radar sensor.

At block 530 of the process 500, a view angle of a mm-wave FMCW radar sensor positioned in the interior of the vehicle or room is adjusted based on the location of the subject's chest and/or body orientation. The view angle may also be referred to as an "elevation angle." Having the mm-wave FMCW radar sensor directed towards the location of the subject's chest increases the performance and reliability of the mm-wave FMCW radar sensor when acquiring cardiovascular or respiratory measurements. To be directed towards the location the subject's chest, the subject's chest may be within a viewing area of the view angle. The mm-wave FMCW radar sensor may obtain optimized cardiovascular or respiratory measurements for signals transmitted within the viewing area. In some implementations, the subject's chest may be within 10 degrees of the radar sensor's view angle to be within the viewing area. In some implementations, the subject's chest may be within 20 degrees of the radar sensor's view angle to be within the viewing area.

The multi-sensor system further includes the mm-wave FMCW radar sensor. The control system may be in electrical communication (directly or indirectly) with the mm-wave FMCW radar sensor. Upon determining the location of the subject's chest and/or the body orientation of the subject, the control system may adjust the view angle of the mm-wave FMCW radar sensor based on the aforementioned determination. The view angle of the mm-wave FMCW radar sensor may be directed at the subject's chest or within a few degrees of the subject's chest.

In some implementations, the process 500 further includes selecting the mm-wave FMCW radar sensor from among a plurality of mm-wave FMCW radar sensors located in the vehicle or room. Multiple mm-wave FMCW radar sensors may be positioned in different locations around the vehicle or room. After determining the body orientation of the subject, one of the mm-wave FMCW radar sensors may be selected. The selected mm-wave FMCW radar sensor may be facing the frontal plane of the subject. By selecting the mm-wave FMCW radar sensor that faces the frontal plane of the subject, the accuracy of cardiovascular or respiratory measurements made by the mm-wave FMCW radar sensor is improved. In some implementations, the selected mm-wave FMCW radar sensor may be more proximate to the subject compared to the other mm-wave FMCW radar sensors. Proximity to the subject for a mm-wave FMCW radar sensor may be within about 5 m or less, about 3 m or less, or about 1 m or less. Generally speaking, performance and reliability of a mm-wave FMCW radar sensor is improved when placed closer to the subject. When the mm-wave FMCW radar sensor is placed too far, not only may the signal be attenuated, but there is a greater chance of some object blocking the path of the signals to prevent the mm-wave FMCW radar sensor from functioning.

At block 540 of the process 500, a first cardiovascular or respiratory measurement is obtained from the mm-wave FMCW radar sensor. The first cardiovascular measurement may be a heartbeat pattern for determining heart rate, and the first respiratory measurement may be a respiration pattern for determining respiration rate. The first cardiovascular or respiratory measurement may be obtained after adjusting the view angle of the mm-wave FMCW radar sensor. The mm-wave FMCW radar sensor may transmit and receive signals having a wavelength in the millimeter range to detect small movements and vibrations. These movements and vibrations may correspond to the subject's heart beats or respiration. Heart beats and human respiration may be distinguished from other motions of the subject. The mm-wave FMCW radar sensor may be positioned in any suitable location in the interior of the vehicle or room. In some implementations, the mm-wave FMCW radar sensor may be positioned on a steering wheel, dashboard, center console, overhead console, seat, top ceiling, rear-view mirror, or windshield in a vehicle. In some other implementations, the mm-wave FMCW radar sensor may be positioned on a wall, ceiling, or stationary object in a room.

At block 550 of the process 500, a second cardiovascular or respiratory measurement from an IMU sensor may be obtained. The second cardiovascular measurement may be a heartbeat pattern for determining heart rate, and the second respiratory measurement may be a respiration pattern for determining respiration rate. The second cardiovascular or respiratory measurement may be obtained simultaneous with the first cardiovascular or respiratory measurement. The IMU sensor may be positioned in the vehicle or room to record motion activity associated with the subject. The motion activity may be indicative of the subject's heart beats or respiration. In some implementations, the IMU sensor may be an accelerometer positioned to record vibrations from the subject's body transferred to another object. Specifically, the IMU sensor may obtain a ballistocardiogram for recording the subject's heartbeat pattern. The IMU sensor may be integrated or disposed on a stationary object in the vehicle or room. The stationary object may be in contact with the subject. In some implementations, the IMU sensor may be positioned inside a seat, positioned on an outer surface of the seat, or positioned underneath the seat. In some implementations, the IMU sensor may be positioned inside a bed, positioned on an outer surface of the bed, or positioned underneath the bed.

The multi-sensor system further includes the IMU sensor. The IMU sensor may include an accelerometer. The control system may be in electrical communication (directly or indirectly) with the IMU sensor. Data from the IMU sensor and data from the mm-wave FMCW radar sensor may be received by the control system and processed by the control system. Data from both the IMU sensor and the mm-wave FMCW radar sensor may record motion activity of the subject. In some implementations, data from the IMU sensor or the mm-wave FMCW radar sensor may include bodily motion artifacts. Data associated with bodily motion artifacts may be identified by the control system and subsequently removed when calculating a cardiovascular or respiratory measurement. Identification and removal techniques of bodily motion artifacts may be done according to statistical approaches known in the art.

In some implementations, the process 500 further includes obtaining internal motion data associated with the vehicle from a second IMU sensor. The internal motion data associated with the vehicle may be limited to internal motion activity occurring within the interior of the vehicle. Such internal motion activity may be caused by bumps, dips, turns, jerks, stops, acceleration, deceleration, and other motions that can cause objects in the interior of the vehicle to move or vibrate. The internal motion activity may be identified as noise or motion artifacts to be subtracted from the first cardiovascular or respiratory measurement or from the second cardiovascular or respiratory measurement. The second IMU sensor may be positioned on the steering wheel, dashboard, center console, overhead console, seat, top ceiling, rear-view mirror, or windshield of the vehicle. The multi-sensor system may further include the second IMU sensor, where the control system may be in electrical communication (directly or indirectly) with the second IMU sensor.

At block 560 of the process 500, the first and second cardiovascular or respiratory measurements are consolidated to obtain an optimal cardiovascular or respiratory measurement. Consolidation may include denoising unwanted noise or motion artifacts unrelated to heart beats or breathing. The control system receives data from the one or more proximity sensors, data from the mm-wave FMCW radar sensor including the first cardiovascular or respiratory measurement, and data from the IMU sensor including the second cardiovascular or respiratory measurement. The data from the mm-wave FMCW radar sensor may have a first associated confidence factor or filter parameter, and the data from the IMU sensor may have a second associated confidence factor or filter parameter. Each associated confidence factor may be based in part on the data itself such as its signal-to-noise ratio. Each associated confidence factor may be based in part on the body orientation of the subject. Depending on how the subject is positioned in the vehicle or room, or depending on if the subject is in direct contact with the object on which the IMU sensor is placed, the mm-wave FMCW radar sensor may be more reliable or the IMU sensor may be more reliable. Each associated confidence factor may be based in part on how the sensors are positioned in the vehicle or room relative to the subject. Depending on if there are intervening objects obstructing the view of the mm-wave FMCW radar sensor, or depending on how proximate the mm-wave FMCW radar sensor or IMU sensor is to the subject, the mm-wave FMCW radar sensor may be more reliable or the IMU sensor may be more reliable. Each associated confidence factor may change over time as context in the vehicle or room changes.

After the first associated confidence factor and the second associated confidence factor are calculated, an algorithm fuses the first and second cardiovascular or respiratory measurements. How aggressively signals are filtered out from a cardiovascular or respiratory measurement depends on an associated confidence factor. The first and second cardiovascular or respiratory measurements are consolidated in a manner so that unwanted noise or motion artifacts are denoised. Furthermore, the first and second cardiovascular or respiratory measurements are consolidated in a manner so that less reliable measurements (i.e., lower associated confidence factors) are more aggressively filtered out and more reliable measurements (i.e., higher associated confidence factors) are more weighted or selected by the algorithm. Accordingly, consolidation denoises motion artifacts and fuses data to obtain a more reliable cardiovascular or respiratory measurement.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor or any conventional processor, controller, microcontroller or state machine. A processor may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, the structures disclosed in this specification and their structural equivalents thereof, or in any combination thereof. Implementations of the subject matter described in this specification may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module that may reside on a computer-readable medium. Computer-readable media include both computer storage media and communication media including any medium that may be enabled to transfer a computer program from one place to another. Storage media may be any available media that may be accessed by a computer. By way of example and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein.

Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

What is claimed is:

1. A multi-sensor system comprising:
a plurality of mm-wave frequency modulated continuous wave (FMCW) radar sensors for obtaining multiple cardiovascular or respiratory measurements from multiple subjects in the interior of a vehicle, each of the cardiovascular or respiratory measurements being calculated to determine a subject's stress level, level of drowsiness, or health;
a first inertial measurement unit (IMU) sensor positioned in the interior of the vehicle, wherein the first IMU sensor is configured to obtain a second cardiovascular or respiratory measurement of at least one subject of the multiple subjects;
a second IMU sensor positioned in the interior of the vehicle, wherein the second IMU sensor is configured to obtain motion data associated with the vehicle;
one or more proximity sensors configured to identify a location of the at least one subject of the multiple subjects chest inside the vehicle; and
a control system communicatively connected to the plurality of mm-wave FMCW radar sensors, wherein the control system is configured to perform an action in the vehicle in response to the at least one subject's of the multiple subjects stress level, level of drowsiness, or health.

2. The multi-sensor system of claim 1, wherein the mm-wave FMCW radar sensor is configured to transmit signals towards the location of the subject's chest.

3. The multi-sensor system of claim 1, wherein the first IMU sensor is positioned in a seat, positioned on an outer surface of the seat, or positioned underneath the seat of the vehicle.

4. The multi-sensor system of claim 1, wherein the second IMU sensor is positioned on a steering wheel or dashboard of the vehicle.

5. The multi-sensor system of claim 1, wherein the mm-wave FMCW radar sensor is positioned in the same or approximately the same location as the second IMU sensor.

6. The multi-sensor system of claim 5, wherein the one or more proximity sensors comprise an array of capacitive proximity sensors.

7. The multi-sensor system of claim 6, wherein the array of capacitive proximity sensors are configured to map at least a portion of an outline of a subject's body to identify the location of the subject's chest.

8. The multi-sensor system of claim 1, further comprising:
a control system communicatively connected to the mm-wave FMCW radar sensor, the first IMU sensor, the second IMU sensor, and the one or more proximity sensors, wherein the control system is configured to:
determine the location of the subject's chest relative to the mm-wave FMCW radar sensor using the one or more proximity sensors; and
adjust a view angle of the mm-wave FMCW radar sensor to be directed towards the location of the subject's chest.

9. The multi-sensor system of claim 8, wherein the control system is further configured to:
consolidate the first cardiovascular or respiratory measurement, the second cardiovascular or respiratory measurement, and the motion data associated with the vehicle to obtain an optimal cardiovascular or respiratory measurement.

10. The multi-sensor system of claim 9, wherein the first cardiovascular or respiratory measurement has a first associated confidence factor and the second cardiovascular or respiratory measurement has a second associated confidence factor, wherein the first and second cardiovascular or respiratory measurements are consolidated according to an algorithm based in part on the first and second associated confidence factors and the motion data associated with the vehicle is subtracted from either the first or second cardiovascular or respiratory measurement to obtain the optimal cardiovascular or respiratory measurement.

* * * * *